United States Patent [19]

Meyer et al.

[11] Patent Number: 5,262,017
[45] Date of Patent: Nov. 16, 1993

[54] PLURAL STAGE PURIFICATION OF PROPYLENE OXIDE

[75] Inventors: Robert A. Meyer, St. Louis, Mo.; William A. Smith, Houston; Mark A. Mueller, Austin, both of Tex.; Gregory B. Demoll, LaGrange Park, Ill.

[73] Assignee: Texaco Chemical Company, White Plains, N.Y.

[21] Appl. No.: 47,910

[22] Filed: Apr. 19, 1993

[51] Int. Cl.⁵ .................... B01D 3/40; C07D 301/32
[52] U.S. Cl. ........................... 203/64; 203/70; 203/74; 203/77; 549/541
[58] Field of Search ............... 203/14, 64, 68, 70, 203/56, 74, 77; 549/541, 542

[56] References Cited

U.S. PATENT DOCUMENTS

| | | | |
|---|---|---|---|
| 3,338,800 | 8/1967 | Binning et al. | 203/70 |
| 3,464,897 | 9/1969 | Jubin | 203/70 |
| 3,578,568 | 5/1971 | Washall | 203/64 |
| 3,607,669 | 9/1971 | Jubin | 203/70 |
| 3,838,020 | 9/1974 | Kageyama et al. | 203/64 |
| 3,843,488 | 10/1974 | Schmidt et al. | 203/70 |
| 4,971,661 | 11/1990 | Meyer et al. | 203/54 |
| 5,000,825 | 3/1991 | Shih et al. | 203/64 |
| 5,133,839 | 7/1992 | Shih et al. | 203/64 |
| 5,139,622 | 8/1992 | Marquis et al. | 203/64 |
| 5,160,587 | 11/1992 | Marquis et al. | 203/64 |

Primary Examiner—Wilbur Bascomb, Jr.
Attorney, Agent, or Firm—James L. Bailey; Kenneth R. Priem; Carl G. Ries

[57] ABSTRACT

Impure propylene oxide is purified by a distillation process wherein it is (a) extractively distilled in a first column using a $C_2$ to $C_6$ alkylene glycol extractive distillation agent to form a first overhead fraction comprising propylene oxide, $C_5$–$C_7$ hydrocarbons methanol, water and oxygen-containing impurities, (b) wherein the first overhead fraction is separated in a second column into a second overhead fraction comprising most of the pentanes, pentenes and oxygen-containing impurities and a partially purified propylene oxide bottoms fraction comprising propylene oxide, hexenes, hexanes, and only residual quantities of pentenes and pentanes, (c) wherein the partially purified bottoms fraction is extracting distilled in a third column using a $C_7$–$C_{10}$ alkane hydrocarbon extractive distillation agent to provide a further purified bottoms fraction containing substantially all of the propylene oxide, hexenes, hexanes charged to the third distillation column, and (d) the further purified bottoms fraction is extractively distilled in a fourth column using a $C_7$ to $C_{10}$ alkane hydrocarbon extractive distillation agent to provide a purified propylene oxide overhead fraction consisting essentially of propylene oxide.

17 Claims, 1 Drawing Sheet

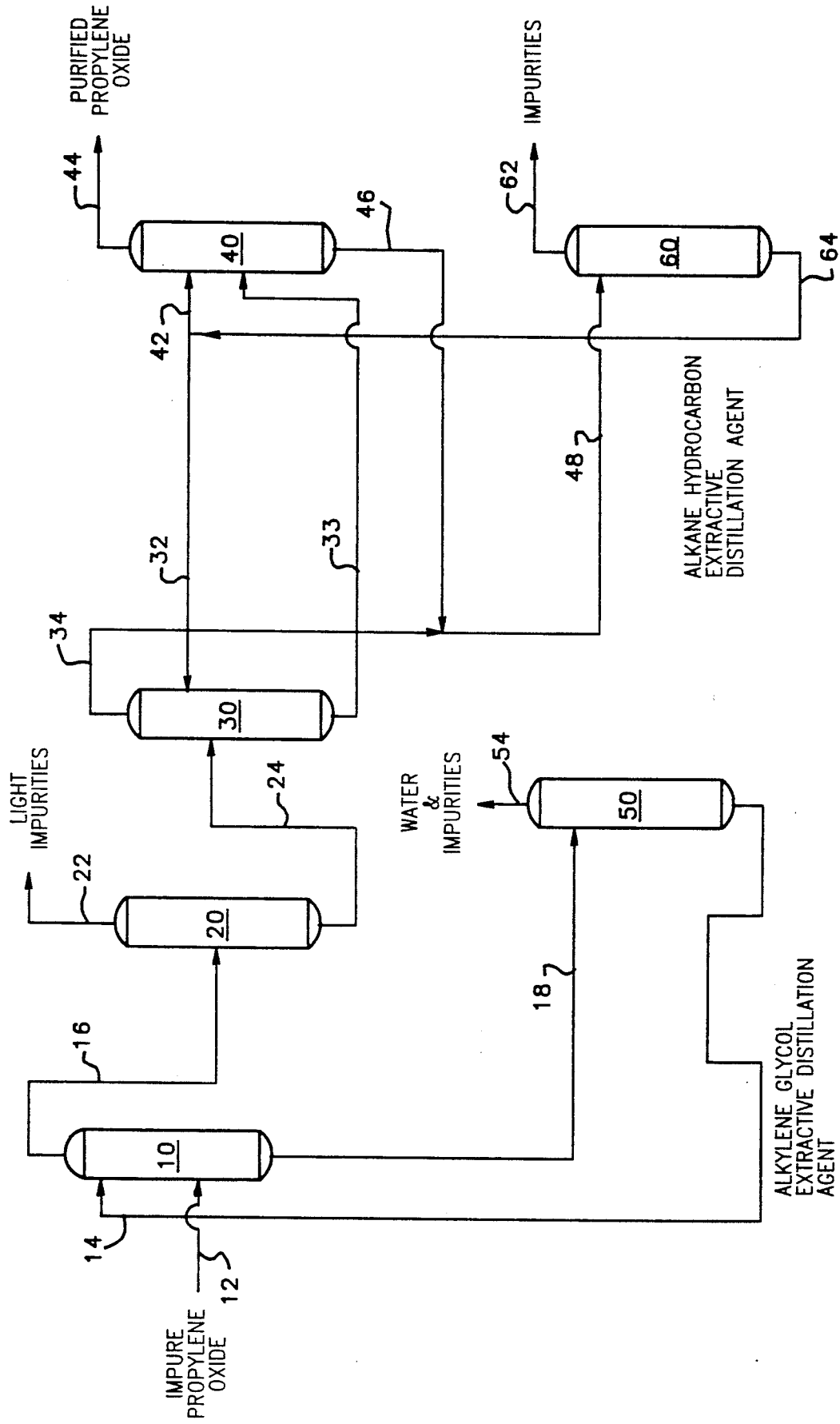

PLURAL STAGE PURIFICATION OF PROPYLENE OXIDE

BACKGROUND OF THE INVENTION

1. Field of the Invention

This invention relates to the plural stage purification of propylene oxide. More particularly, this invention relates to a plural stage distillation process for removing contaminating quantities of impurities from propylene oxide. Still more particularly, this invention relates to a plural stage distillation process for the purification of impure propylene oxide contaminated with impurities including water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate. The impure propylene oxide is distilled by a plural stage process using a $C_2$ to $C_6$ alkylene glycol extractive distillation agent and a $C_7$ to $C_8$ alkane hydrocarbon extractive distillation agent.

2. Prior Art

It is known to use alkane hydrocarbons containing 6 to 18 carbon atoms as extractive distillation agents in the purification of propylene oxide. See, for example, Binning et al. U.S. Pat. No. 3,338,800, Jubin U.S. Pat. No. 3,464,897, Jubin U.S. Pat. No. 3,607,669 and Schmidt U.S. Pat. No. 3,843,488. Jubin U.S. Pat. No. 3,464,897 shows that an alkane such as octane is effective for the removal of 6 carbon atom alkane impurities such as 2-methyl pentane, 4-methyl pentene-1, 2-methyl pentene-1 and 2-methyl pentene-2. Schmidt U.S. Pat. No. 3,843,488 shows that alkanes containing from 8 to 20 carbon atoms, and preferably from 8 to 10 carbon atoms, such as n-octane, is effective for removing hydrocarbon impurities containing 5 to 7 hydrocarbons from propylene oxide.

It is also known to use alkylene glycols containing from 2 to 6 carbon atoms as extractive distillation agents in the purification of propylene oxide. See, for example, Washall U.S. Pat. No. 3,578,568, Kageyama et al. U.S. Pat. No. 3,838,020, Shih et al. U.S. Pat. No. 5,000,825, Marquis et al. U.S. Pat. No. 5,139,622, and Marquis et al. U.S. Pat. No. 5,160,587. Thus, Washall U.S. Pat. No. 3,578,568 discloses the use of ethylene glycol and propylene glycol as extractive agents for the purification of propylene oxide. Kageyama et al. U.S. Pat. No. 3,838,020 discloses the use of butylene glycols for this purpose. Shih et al. U.S. Pat. No. 5,000,825 discloses the use of glycols containing 2 to 4 carbon atoms such as ethylene glycol, propane diol, butane diol, etc. Marquis et al. U.S. Pat. No. 5,139,622 discloses the use of triethylene glycol as an extractive distillation agent and Marquis et al. U.S. Pat. No. 5,160,587 discloses the use of dipropylene glycol as an extractive distillation agent.

The use of plural stage distillation for the purification of propylene oxide has also been proposed.

Schmidt U.S. Pat. No. 3,881,996 discloses a plural stage process for the purification of propylene oxide including a first fractionation wherein light impurities such as acetaldehyde are removed overhead followed by a second distillation step wherein heavy impurities such as propionaldehyde are removed in order to provide a second distillate fraction which is then extractively distilled in the presence of octane in a third distillation zone to provide pure propylene oxide and to remove alkane hydrocarbon impurities such as $C_6$ carbon atom impurities from the propylene oxide. Schmidt et al. teach that it is important to use the proper sequence of distillation steps and that, for example, removal of heavy impurities such as propionaldehyde before the removal of light impurities such as acetaldehyde will lead to adverse results.

Shih U.S. Pat. No. 5,133,839 discloses a plural stage process for the purification of propylene oxide utilizing a conventional distillation zone which preferably contains two distillation columns, as in Schmidt U.S. Pat. No. 3,881,996, followed by extractive distillation of the parts of purified propylene oxide in two sequential extractive distillation columns using either isoctane or a lower alkylene glycol as the extractive distillation agent and removing lighter impurities in the first of the extractive distillation columns and heavier impurities from the second of the extractive distillation columns.

Meyer et al. U.S. Pat. No. 4,971,661 discloses a plural stage process for the purification of propylene oxide, but different extractive distillation agents such as water and acetone are used.

BACKGROUND INFORMATION

As illustrated by the prior art just discussed, it was known prior to the present invention to use plural stage distillation for the purification of propylene oxide and to use lower alkylene glycols and higher alkanes as extractive distillation agents. Thus, it was known that the use of the 8 to 10 carbon atom alkanes as extractive distillation agents was particularly effective for removing contaminating quantities of hydrocarbons such as hydrocarbons containing 5 to 7 carbon atoms from propylene oxide. It was also known to use the lower alkylene glycols, which are polar solvents, for the extractive distillation in order to remove oxygenated impurities.

Pentanes and pentenes are present in crude propylene oxide as minor impurities. It has been discovered in accordance with the present invention that the removal of pentane and pentenes presents a difficult problem.

Thus, as is pointed out, for example by Schmidt U.S. Pat. No. 3,881,996, the sequence of distillation steps employed in the plural stage purification of propylene oxide is crucial to effective purification. Reversing or otherwise altering the sequence of steps can lead to adverse results.

Pentanes, isopentane and pentenes may be removed like other hydrocarbon impurities by using octane in an extractive distillation. The octane lowers the relative volatility of the hydrocarbons relative to propylene oxide. However, the degree of relative volatility change is proportional to the amount of octane solvent present. Using typical solvent to feed ratios as disclosed in the prior art and in this invention, it has been discovered that pentanes and pentenes are not easily removed and tend to remain in the PO product. Therefore, this invention discloses that a more economical and efficient means of removing pentanes and pentenes is by a conventional distillation upstream of the octane extractive distillation. The C5 stripper tower should not be located downstream of the octan extractive distillation since the final PO product would then be a bottoms product off the stripper. It is advantageous to take high purity products off the top of columns rather than off the bottom.

Thus, when partially purified propylene oxide containing contaminating quantities of 5 to 7 carbon atom hydrocarbons such as pentanes, pentenes, hexanes, hexenes, heptanes and heptenes is subjected to extractive distillation using an alkane hydrocarbon extractive distillation agent such as octane, a significant portion of the pentanes and pentenes will remain with the overhead purified propylene oxide rather than being removed therefrom for withdrawal from the bottom of the tower together with the extractive distillation agent and the other impurities. As a consequence, a subsequent distillation step would normally be required for the removal of the pentanes and pentenes.

It has been discovered in accordance with the present invention, however, that the use of a different sequence of distillation steps from that disclosed in the prior art will obviate this problem so that there is no need for an additional distillation tower downstream of the alkane hydrocarbon extractive distillation.

SUMMARY OF THE INVENTION

In accordance with the present invention, impure propylene oxide is separated from contaminating quantities of hexanes, hexenes, pentanes, pentenes, and oxygen-containing impurities by a sequential extractive distillation process wherein the impure propylene oxide is first extractively distilled using a lower alkylene glycol extractive distillation agent to form a first overhead fraction comprising propylene oxide, hexanes, hexenes, pentanes and pentenes and oxygen-containing impurities boiling above propylene oxide, wherein the first overhead distillation fraction is separated in a second distillation column into a second overhead distillation fraction comprising most of the pentanes, pentenes, oxygen-containing impurities boiling above propylene oxide and a residual amount of propylene oxide and a partially purified propylene oxide bottoms fraction comprising propylene oxide, hexenes, hexanes and only residual quantities of pentenes and pentanes, wherein the partially purified bottoms fraction is extractively distilled in a third distillation column using a $C_7$-$C_8$ alkane hydrocarbon extractive distillation agent to provide a further purified bottoms fraction containing substantially all of the propylene oxide, hexenes, hexanes and pentenes charged to the third distillation column and wherein the partially purified propylene oxide bottoms fraction is further purified in an extractive distillation column using a $C_7$-$C_8$ alkane hydrocarbon extractive distillation agent to provide a pure propylene oxide overhead fraction consisting essentially of propylene oxide.

In accordance with a preferred embodiment of the present invention, impure propylene oxide contaminated with pentanes, pentenes, hexenes, hexanes and oxygen-containing impurities is purified by a sequential extractive distillation process wherein (a) the impure propylene oxide is extractively distilled using a first $C_2$ to $C_6$ alkylene glycol extractive distillation agent to form a first lighter distillation fraction containing all of the propylene oxide, hexenes, hexanes, pentenes and pentanes and oxygen-containing impurities boiling above propylene oxide and a first heavier distillation fraction containing water and oxygen-containing impurities boiling below propylene oxide and all of the first extractive distillation agent, wherein (b) the first lighter distillation fraction is separated in a second distillation column into a second lighter distillation fraction containing most of the pentanes, pentenes, oxygen-containing impurities boiling above propylene oxide and a residual amount of propylene oxide and a second heavier distillation fraction containing substantially all of the propylene oxide, hexenes, hexanes and only residual quantities of pentenes and pentanes, wherein (c) the second heavier distillation fraction is extractively distilled using a $C_7$ to $C_8$ alkene hydrocarbon extractive distillation agent to provide a third lighter distillation fraction containing residual oxygen-containing impurities and water and a third heavier distillation fraction containing substantially all of the propylene oxide, hexenes, hexanes and residual pentanes in an extractive distillation agent and wherein (d) the third heavier distillation fraction is extractively distilled using a $C_7$ to $C_8$ alkane extractive distillation agent to provide a fourth lighter distillation fraction consisting essentially of pure propylene oxide and a fourth heavier distillation fraction containing all of the extractive distillation agent, all the hexenes, hexanes and also residual quantities of propylene oxide, pentenes and pentanes.

In accordance with the preferred embodiment of the present invention, a distillation process is provided for the purification of impure propylene oxide contaminated with water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate comprising the steps of:

a. Charging the impure propylene oxide to a first extractive distillation column;

b. Charging a lower alkylene glycol extractive distillation agent to the first extractive distillation column at a feed point above the point of introduction of the impure propylene oxide;

c. Fractionating the impure propylene oxide in the first extractive distillation column under distillation conditions selected to provide a first lighter distillation fraction containing all of the propylene oxide, propylene, propane, acetaldehyde, methyl formate, hexenes, hexanes, pentenes and pentanes and a portion of the methanol and water and also a first heavier distillation fraction containing all of the propionaldehyde, acetone, t-butyl alcohol, t-butyl formate, isopropyl alcohol and the remainder of the methanol and water and all of the extractive distillation agent;

d. Charging a second feedstock comprising the first lighter distillation fraction to a second distillation column;

e. Fractionating the second feedstock in the second distillation column under distillation conditions selected to provide a second lighter distillation fraction containing all of the propylene, propane, acetaldehyde, pentanes, pentenes and a residual amount of propylene oxide and a second heavier distillation fraction containing substantially all of the propylene oxide, hexenes, hexanes and only a residual quantity of pentenes and pentanes;

f. Charging a third feedstock comprising the heavier distillation fraction to a third extractive distillation column;

g. Charging a $C_7$ to $C_8$ alkane hydrocarbon extractive distillation agent to the third extractive distillation column at a feed point above the point of introduction of the third feedstock;

h. Fractionating the third feedstock in the third extractive distillation column under distillation conditions selected to provide a third lighter distillation fraction containing all of the acetaldehyde, methyl formate, methanol, water and residual quantities of propylene oxide and hexane and a third heavier distillation fraction containing substantially all of the propylene oxide and extractive distillation agent charged to the third distillation column in all of the hexenes and hexanes charged to the third distillation column;

i. Charging a fourth feedstock comprising the third heavier distillation fraction to a fourth extractive distillation column;

j. Charging a $C_7$ to $C_8$ alkene hydrocarbon extractive distillation agent to the fourth extractive distillation column at a feed point above the point of introduction of the third feedstock; and k. Fractionating said fourth feedstock in the fourth extractive distillation column under distillation conditions selected to provide a fourth lighter distillation fraction consisting essentially of pure propylene oxide, and a fourth heavier distillation fraction containing substantially all of the extractive distillation agent, all the hexenes and hexanes and also the residual quantities of propylene oxide, pentenes and pentanes

BRIEF DESCRIPTION OF THE DRAWING

The drawing is a schematic flow sheet with conventional parts omitted showing the general recovery sequence that is used in accordance with the present invention to purify propylene oxide.

DESCRIPTION OF THE PREFERRED EMBODIMENT

Turning now to the drawing, there is shown a schematic flow sheet illustrating a preferred method for practicing the process of the present invention. In the drawing, conventional parts such as valves, pumps, temperature sensors, pressure sensors, heaters, coolers, flow control regulation apparatus, reboilers, reflux condensers, etc., have been omitted.

The impure propylene oxide to be purified in accordance with the present invention is typically propylene oxide prepared by the reaction of tertiary butyl hydroperoxide with propylene in the presence of a molybdenum catalyst to provide a reaction mixture comprising unreacted propylene, unreacted tertiary butyl hydroperoxide, tertiary butyl alcohol, propylene oxide, and impurities. This reaction product is separated in a distillation zone (not shown) into a plurality of fractions including a propylene recycle fraction, an impure propylene oxide fraction, a tertiary butyl alcohol fraction and a residue fraction.

The impure propylene oxide obtained in this fashion is suitably used as a feedstock for the present invention and will normally be contaminated with impurities including water, propylene, propane, acetaldehyde, methyl formate, propionaldehyde, hexenes, acetone, hexanes, methanol, tertiary butyl alcohol, pentane, isopentane (i.e., crude ash methyl butane), pentenes, isopropyl alcohol and tertiary butyl formate.

The impure propylene oxide will normally contain from about 97 to about 99 wt.% of propylene oxide, the balance being impurities such as those enumerated above. It will be understood that some of the enumerated impurities will not always be present in impure propylene oxide and that other impurities not listed may be present in minor quantities. The impurities, broadly speaking, comprise water, hydrocarbons such as propylene, propane, hexenes, hexanes, pentane, isopentane and pentenes, and oxygenated impurities including aldehydes, alcohols, esters, etc. The hydrocarbon impurities will normally contain from about 2 to about 6 carbon atoms and the oxygenated impurities will normally contain from about 2 to about 6 carbon atoms also.

In accordance with the present invention, an impure propylene oxide of the type described is charged to a first extractive distillation column 10 by way of a charge line 12. The fractional distillation column 10 may suitably comprise from about 40 to about 80 theoretical trays and the charge line 12 for the impure propylene oxide will normally be at least about 10 to about 30 trays from the bottom of the distillation tower.

An alkylene glycol extractive distillation agent is also charged to the line 10 by a line 14. The alkylene glycol extractive distillation agent may suitably be an alkylene glycol containing from 2 to 6 carbon atoms such as ethylene glycol, propylene glycol, 1,4-propane diol, 1,3-2-methyl propane diol, 1,4-butane diol, 2-methyl-1,3-propane diol, diethylene glycol, triethylene glycol, dipropylene glycol, etc. Preferred extractive distillation agents include triethylene glycol and dipropylene glycol.

The alkylene glycol extractive agent 14 will suitably be charged to the extractive distillation column 10 in the ratio of about 2 to 7 parts of impure propylene oxide per part of alkylene glycol extractive distillation agent.

Extractive distillation conditions are adjusted in the extractive distillation tower 10 so as to provide for the recovery overhead or as a distillate fraction of substantially all of the propylene oxide charged to the extractive distillation column 10. For example, the impure propylene oxide, which will suitably comprise about 98.5 wt.% propylene oxide, the balance being impurities as mentioned above, may be charged at a temperature of about 100° F. to about 160° F.

The temperature at the bottom of the extractive distillation column 10 may suitably be about 300°–380° F. and the pressure may be about 20–50 psia. The temperature at the top of the extractive distillation column 10 may, for example, be about 90°–130° F. and the pressure may suitably be about 10–30 psia. A first lighter distillation fraction comprising impure propylene oxide is removed from the column 10 by way of a line 16 and may suitably comprise more than 99 wt.% propylene oxide, the balance being impurities including acetaldehyde, methyl formate, hexenes, hexanes, methanol, water, pentanes, isopentanes and pentenes. A heavier distillation fraction 18 discharged adjacent the bottom of the extractive distillation column 10 will comprise impurities including water, propionaldehyde, acetone, methanol, tertiary butyl alcohol, isopropyl alcohol, tertiary butyl formate and the alkylene glycol extractive distillation agent.

A second feedstock comprising the first lighter distillation fraction 16 is charged to a second distillation column 20 which may suitably contain from about 20 to about 40 theoretical trays, the second feedstock being suitably charged to about 8 to about 16 theoretical trays from the bottom of the tower. Distillation conditions are adjusted in the distillation column 20 to provide a second lighter distillation fraction discharged by way of a line 22 and a second heavier distillation fraction discharged by a line 24. Distillation conditions are suitably adjusted in the distillation column 20 so that substantially all of the propylene oxide will be present in the second heavier distillation fraction 24. Typically, the lighter distillation fraction 22 will comprise impurities including propylene, propane, acetaldehyde and, significantly, substantially all of the pentanes and pentenes charged to the distillation column 20. The second heavier distillation fraction will typically contain substantially all of the propylene oxide, hexenes, hexanes and only residual quantities of pentanes and pentenes.

A third feedstock comprising the second heavier distillation fraction 24 is charged to a third distillation column 30 together with a $C_7$ to $C_8$ alkane hydrocarbon extractive distillation agent which is charged by a line 32.

The alkane extractive distillation agent may suitably be charged to the third distillation column 30 in the ratio of about 5 to about 7 parts of extractive distillation agent per part of third feedstock 24. Extractive distillation conditions are adjusted in the distillation column 30 to provide for a fourth heavier distillation fraction 33 containing substantially all of the propylene oxide, hexenes, hexanes, and residual pentenes and pentanes and a lighter distillation fraction 34 which will typically comprise impurities such as methyl formate, acetaldehyde, water and methanol. Residual quantities of propylene oxide and hexane may also be present.

The extractive distillation agent charged to the distillation column 30 is suitably an 8 carbon atom alkane such as normal octane or isooctane. A minor amount of an alkane such as nonane (usually less than 1 wt.%) may also be present in the extractive distillation agent charged to the extractive distillation tower 30 by the line 32. The third feedstock 24 charged to the third distillation column 30 may be suitably charged at a temperature of about 130°-180° F. The temperature at the bottom of the extractive distillation column 30 may suitably be about 180°-220° F. and the pressure may suitably be about 30-50 psia. The temperature adjacent the top of the extractive distillation tower 30 may suitably be about 130°-160° F. and the pressure may suitably be about 20-40 psia.

A fourth feedstock comprising the third heavier distillation fraction 33 is charged to a fourth extractive distillation tower 40 together with an alkane extractive distillation agent such as octane which is charged by way of a line 42. The extractive distillation agent 42 may be charged to the extractive distillation column 40 in the ratio of about 0.4 to about 0.8 parts of extractive distillation agent per part of fourth feedstock 33.

Distillation conditions are adjusted in the distillation column 40 to provide lighter distillation fraction 44 consisting essentially of propylene oxide and a heavier distillation fraction 46 comprising the hexenes, hexanes, residual pentenes, residual pentanes and the extractive distillation agent.

Suitably, the temperature at the top of the distillation column 40 may be about 100°-130° F. and the pressure may be about 10-30 psia. The temperature adjacent the bottom of the distillation column 40 may suitably be about 250°-290° F. and the pressure may suitably be about 25-45 psia.

A fifth feedstock comprising the first heavier distillation fraction 18 from the first distillation column 10 may be charged to a fifth distillation column 50 containing from about 20 to about 60 theoretical trays wherein the fifth feedstock may be separated under distillation conditions adjusted to provide for the recovery of substantially all of the alkylene glycol extractive distillation agent as a heavier distillation fraction discharged from the distillation column by a line 14 and a lighter distillation fraction 54 discharged from the distillation column 50 and suitably containing substantially all of the water, acetone, tertiary butyl alcohol, methanol and isopropyl alcohol contained in the fifth feedstock 18.

The pressure at the top of the fifth distillation column 50 may suitably be about 0.1-1.0 psia and the temperature may suitably be about 90°-130° F. The pressure at the bottom of the distillation column 50 may suitably be about 0.1-1.1 psia and the temperature may suitably be about 300°-360° F.

A sixth feedstock comprising the third lighter distillation fraction 34 and the fourth heavier distillation fraction 46 may suitably be charged by way of a line 48 to a sixth distillation column 60 which may comprise, for example, from about 30 to about 50 theoretical trays and wherein the sixth feedstock is introduced at least about 20 theoretical trays from the bottom of the column. Distillation conditions are adjusted within the distillation column 60 to provide for the recovery of a sixth lighter distillation fraction 62 comprising acetaldehyde, methyl formate, propylene oxide, hexenes, methanol and a minor amount of octane and a sixth heavier distillation fraction 64 comprising substantially all of the extractive distillation agent charged to the distillation column 60 by the line 48. For example, the distillation conditions established in the sixth distillation column 60 may include a pressure at the top of the column of about 15-30 psia and a temperature of about 100°-140° F. and a pressure at the bottom of the column of about 20-40 psia and a temperature of about 200°-300° F.

EXAMPLES

The invention will be further illustrated by the following specific example which is given by way of illustration and not as a limitation on the scope of this invention. Where parts are mentioned, they are parts by weight.

About 1000 parts of an impure propylene oxide feedstock 12 containing about 98.5 wt.% of propylene oxide and contaminated with impurities including water, propylene, propane, acetaldehyde, methyl formate, propionaldehyde, hexenes, acetone, hexanes, methanol, t-butyl alcohol, n-pentane, isopentane (i.e., 2-methyl butane), pentene, isopropyl alcohol and tertiary butyl formate and separated under the extractive distillation conditions in the presence of a triethylene glycol extractive distillation agent into a first lighter distillation fraction 16 (about 986 parts) containing more than about 99 wt.% of propylene oxide and less than about 1 wt.% of contaminants including propylene, propane, acetaldehyde, methyl formate, hexenes, hexanes, pentenes, pentanes, water and methanol and a first heavier distillation fraction containing water, propionaldehyde, acetone, tertiary butyl alcohol, tertiary butyl formate, isopropyl alcohol, methanol and the alkylene glycol and the triethylene glycol extractive distillation agent. The first heavier distillation fraction 18 is separated in fifth distillation column 50 into a heavier fraction 14 comprising the triethylene glycol extractive distillation agent which is recycled to the extractive distillation column 10 and a lighter overhead fraction 54 comprising water, acetone, tertiary butyl alcohol, methanol and isopropyl alcohol.

A second feedstock comprising the lighter distillation fraction 16 is separated in the second distillation column 20 into about 985 parts of a heavier distillation fraction 24 and about 1 part of a lighter distillation fraction 22 containing propylene, propane, acetaldehyde, pentenes and pentanes charged to the extractive distillation column 10 by the line 12.

A second heavier distillation fraction 24 discharged from the distillation column 20 will comprise substantially all of the propylene oxide, hexenes, hexanes and only residual quantities of pentanes and pentenes. This fraction is charged by way of the line 24 to a third distillation column 30 together with about 5620 parts of octane charged to the distillation column 30 by a line 32. The distillation column 30 is operated in the manner described above to provide a lighter distillation fraction 34 (about 1 part) and a heavier distillation fraction 33 (about 6604 parts). The fraction 34 will comprise acetaldehyde, methyl formate, methanol, water and residual quantities of propylene oxide and hexane. The third heavier distillation fraction 33 will comprise propylene oxide and substantially all of the octane charged to the third distillation column 30.

A fourth feedstock comprising a third heavier distillation fraction 33 is charged to the fourth extractive distillation column 40 where it is separated together with about 3690 parts of octane in the manner described above into about 985 parts of an overhead distillation fraction consisting essentially of propylene oxide and containing very low quantities of the impurities present in the feedstock charged by the line 12 to the first distillation column 10. A heavier distillation fraction 46 discharged from the column 40 will comprise about 9309 parts of octane, hexenes, hexanes and residual quantities of propylene oxide.

Having thus described our invention, what is claimed is:

1. A process for separating contaminating quantities of hexenes, hexanes, pentenes, pentanes, water and oxygen-containing impurities from impure propylene oxide which comprises:
    extractively distilling the impure propylene oxide in a first distillation column using a $C_2$ to $C_6$ alkylene glycol extractive distillation agent to form a first overhead fraction comprising propylene oxide, hexenes, hexanes, pentenes, pentanes, water, methanol and oxygen-containing impurities boiling above propylene oxide;
    fractionating the first overhead fraction in a second distillation column to obtain a second overhead fraction comprising essentially all of the pentanes and pentenes and most of the oxygen-containing impurities boiling above propylene oxide and a partially purified propylene oxide bottoms fraction comprising propylene oxide, hexenes, hexanes, and only residual quantities of pentenes and pentanes;
    extractively distilling the partially purified bottoms fraction in a third distillation column using a $C_7$ to $C_{10}$ alkane hydrocarbon extractive distillation agent to provide a further purified bottoms fraction comprising substantially all of the propylene oxide, hexenes and hexanes charged to the third distillation column; and
    extractively distilling the further purified bottoms fraction in a fourth distillation column using a $C_7$ to $C_{10}$ alkane hydrocarbon extractive distillation agent to provide a purified propylene oxide overhead fraction consisting essentially of propylene oxide free of said contaminants.

2. A distillation process for the purification of an impure propylene oxide contaminated feedstock with hexenes, hexanes, pentanes, pentenes, water and oxygen-containing impurities which comprises the steps of:
    separately charging said impure propylene oxide feedstock and a $C_2$ to $C_6$ alkylene glycol extractive distillation agent to a first extractive distillation column at ascending charge points, and separating said impure propylene oxide therein into a first lighter distillation fraction containing residual methanol and water and all of the propylene oxide, hexenes, hexanes, pentenes and pentanes and oxygen-containing impurities boiling with and above propylene oxide and a first heavier distillation fraction containing oxygen-containing impurities boiling below propylene oxide and all of the extractive distillation agent,
    charging a second feedstock comprising said first lighter distillation fraction to a second distillation column and separating it therein into a second lighter distillation fraction containing most of the pentanes and pentenes, oxygen-containing impurities boiling above propylene oxide, and a second heavier distillation fraction containing substantially all of the propylene oxide, methanol, water, hexenes, hexanes, and only residual quantities of pentenes and pentanes,
    separately charging a third feedstock comprising said second heavier distillation fraction and a $C_7$ to $C_{10}$ alkane hydrocarbon extractive distillation agent to a third extractive distillation column at ascending charge points and fractionating them therein into a third lighter distillation fraction containing methanol, water and oxygen-containing impurities boiling above propylene oxide, and a third heavier distillation fraction containing substantially all of the propylene oxide, hexenes and hexanes, and extractive distillation agent charged to said third distillation column,
    separately charging a fourth feedstock comprising said third heavier distillation fraction and a $C_7$ to $C_{10}$ alkane hydrocarbon extractive distillation agent to a fourth extractive distillation column at ascending charge points and fractionating it therein into a fourth lighter distillation fraction consisting essentially of propylene oxide and a fourth heavier distillation fraction containing substantially all of the extractive distillation agent, all of the hexenes and hexanes charged to said third distillation column, and also residual quantities of propylene oxide.

3. A distillation process for the purification of an impure propylene oxide contaminated feedstock with impurities including water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate which comprises the steps of:
    charging said impure propylene oxide feedstock to a first extractive distillation column,
    charging a $C_2$ to $C_6$ alkylene glycol extractive distillation agent to said first extractive distillation column at a feed point above the point of introduction of said impure propylene oxide,
    fractionating said impure propylene oxide in said first extractive distillation column under distillation conditions selected to provide a first lighter distillation fraction containing all of the propylene oxide, propylene, propane, acetaldehyde, methyl formate, hexenes, hexanes, pentenes and pentanes, and a portion of the methanol and water and a first heavier distillation fraction containing all of the propionaldehyde, acetone, t-butyl alcohol, t-butyl formate, isopropyl alcohol, the remainder of the methanol and water and all of the extractive distillation agent, charging a second feedstock comprising said first lighter distillation fraction to a second distillation column, fractionating said second feedstock in said second distillation column under distillation conditions selected to provide a second lighter distillation fraction containing all of the propylene, propane, acetaldehyde, pentanes and pentenes, and a residual amount of propylene oxide, and a second heavier distillation fraction containing substantially all of the propylene oxide, hexenes, hexanes, and only residual quantities of pentenes and pentanes, charging a third feedstock comprising said second heavier distillation fraction to a third extractive distillation column, charging a $C_7$ to $C_{10}$ alkane hydrocarbon extractive distillation agent to said third extractive distillation column at a feed point above the point of introduction of said third feedstock, fractionating said third feedstock in said third extractive distillation column under distillation conditions selected to provide a third lighter distillation fraction containing all of the acetaldehyde, methyl formate, methanol and water and residual quantities of propylene oxide and octane, and a third heavier distillation fraction containing substantially all of the propylene oxide and extractive distillation agent charged to said third distillation column and all of the hexenes and hexanes charged to said third distillation column, charging a fourth feedstock comprising said third heavier distillation fraction to a fourth extractive distillation column, charging a $C_7$ to $C_{10}$ alkane hydrocarbon extractive distillation agent to said fourth extractive distillation column at a feed point above the point of introduction of said third feedstock, fractionating said fourth feedstock in said fourth extractive distillation column under distillation conditions selected to provide a fourth lighter distillation fraction consisting essentially of propylene oxide and a fourth heavier distillation fraction containing substantially all of the extractive distillation agent, all of the hexenes and hexanes charged to said third distillation column, and also residual quantities of propylene oxide.

4. A method as in claim 3 wherein the pressure maintained at the top of the first distillation column is about 10-30 psia, wherein the temperature maintained at the top of the first distillation column is about 90°130° F., wherein the pressure maintained at the bottom of the first distillation column is about 20-50 psia, and wherein the temperature maintained at the bottom of the first distillation column is about 300°-380° F.

5. A method as in claim 3 wherein the pressure maintained at the top of the second distillation column is about 35-45 psia, wherein the temperature maintained at the top of the second distillation column is about 110°-130° F., wherein the pressure maintained at the bottom of the second distillation column is about 40-50 psia, and wherein the temperature maintained at the bottom of the second column is about 150°-160° F.

6. A method as in claim 3 wherein the pressure maintained at the top of the third distillation column is about 20-40 psia, wherein the temperature maintained at the top of the third distillation column is about 130°-160° F., wherein the pressure maintained at the bottom of the third distillation column is about 30-50 psia, and wherein the temperature maintained at the bottom of the third distillation column is about 180°-220° F.

7. A method as in claim 3 wherein the pressure maintained at the top of the fourth distillation column is about 10-30 psia, wherein the temperature maintained at the top of the fourth distillation column is about 100°-130° F., wherein the pressure maintained at the bottom of the fourth distillation column is about 25-45 psia, and wherein the temperature maintained at the bottom of the fourth distillation column is about 250°-290° F.

8. A method as in claim 3 wherein the first distillation column contains about 40 to about 80 theoretical trays, wherein the first feedstock is introduced at least about 10 trays from the bottom of the column, wherein the first extractive distillation agent is introduced at least about 30 theoretical trays above the tray at which the first feedstock is introduced, and wherein the weight ratio of first feedstock to the first extractive distillation agent is about 2 to about 7.

9. A method as in claim 3 wherein the second distillation column contains about 20 to about 40 theoretical trays, and wherein the second feedstock is introduced at least about 8 trays from the bottom of the column.

10. A method as in claim 3 wherein the third distillation column contains about 50 to about 80 theoretical trays, wherein the third feedstock is introduced at least about 30 trays from the bottom of the column, wherein the third extractive distillation agent is introduced at least about 10 theoretical trays above the tray at which the third feedstock is introduced, and wherein the ratio of third feedstock to the third extractive distillation agent is about 0.1 to about 0.3.

11. A method as in claim 3 wherein the fourth distillation column contains about 40 to about 80 theoretical trays, wherein the fourth feedstock is introduced at least about 3 trays from the bottom of the column, wherein the fourth extractive distillation agent is introduced at least about 15 theoretical trays above the tray at which the fourth feedstock is introduced, and wherein the ratio of fourth feedstock to the fourth extractive distillation agent is about 1.3 to about 2.2.

12. A method as in claim 3 wherein a fifth feedstock comprising said first heavier distillation fraction is charged to a fifth distillation column wherein:

said fifth feedstock is fractionated in said fifth distillation column under distillation conditions selected to provide a fifth lighter distillation fraction containing substantially all of the water, acetone, t-butyl alcohol, methanol and isopropyl alcohol charged to the fifth distillation column and a fifth heavier distillation fraction containing substantially all of the alkylene glycol extractive distillation agent charged to the fifth distillation column, and wherein said fifth heavier distillation fraction is recycled to said first distillation column as said first extractive distillation agent.

13. A method as in claim 12 wherein the pressure maintained at the top of the fifth distillation column is about 0.1-1.0 psia, wherein the temperature maintained at the top of the fifth distillation column is about 90°-130° F., wherein the pressure maintained at the bottom of the fifth distillation column is about 0.1-1.1 psia, and wherein the temperature maintained at the bottom of the fifth distillation column is about 300°-360° F.

14. A method as in claim 13 wherein the fifth distillation column contains about 10 to about 30 theoretical trays, and wherein the sixth feedstock is introduced at least about 10 trays from the bottom of the column.

15. A method as in claim 3 wherein a sixth feedstock comprising said third lighter distillation fraction and said fourth heavier distillation fraction is charged to sixth distillation column, and wherein said sixth feedstock is fractionated in said sixth distillation column under distillation conditions selected to provide a sixth lighter distillation fraction containing substantially all of the acetaldehyde, methyl formate, propylene oxide, hexenes, methanol, water and a minor portion of the octane charged to the sixth distillation column and a sixth heavier distillation fraction containing substantially all of the $C_7$ to $C_8$ alkane extractive distillation agent charged to the third and fourth distillation columns, and wherein said sixth heavier distillation fraction is recycled to said third and fourth distillation columns as said third and fourth extractive distillation agents.

16. A method as in claim 15 wherein the pressure maintained at the top of the sixth distillation column is about 15-30 psia, wherein the temperature maintained at the top of the sixth distillation column is about 110°-140° F., wherein the pressure maintained at the bottom of the sixth distillation column is about 20-40 psia, wherein the temperature maintained at the bottom of the sixth distillation column is about 200°-300° F.

17. A method as in claim 15 wherein the sixth distillation column contains about 30 to about 50 theoretical trays, and wherein the sixth feedstock is introduced at least about 20 trays from the bottom of the column.

* * * * *